(12) United States Patent  
Masyada

(10) Patent No.: US 8,371,169 B1  
(45) Date of Patent: *Feb. 12, 2013

(54) METALLURGIC TREATMENT AND VERIFICATION SYSTEM

(76) Inventor: Francis Masyada, Largo, FL (US)

( * ) Notice: Subject to any disclaimer, the term of this patent is extended or adjusted under 35 U.S.C. 154(b) by 908 days.

This patent is subject to a terminal disclaimer.

(21) Appl. No.: 12/284,752

(22) Filed: Sep. 25, 2008

Related U.S. Application Data

(63) Continuation-in-part of application No. 11/651,152, filed on Jan. 9, 2007, now Pat. No. 7,464,593, which is a continuation-in-part of application No. 11/008,327, filed on Dec. 9, 2004, now abandoned.

(51) Int. Cl.
  *G01N 29/00* (2006.01)
  *F25D 25/00* (2006.01)
(52) U.S. Cl. .......... 73/579; 73/630; 62/62; 62/311
(58) Field of Classification Search ............ 73/597, 73/579, 618, 627, 630; 62/62, 304, 311; 392/407

See application file for complete search history.

(56) References Cited

U.S. PATENT DOCUMENTS

| | | | |
|---|---|---|---|
| 4,036,598 A | 7/1977 | Soldate | |
| 4,114,421 A * | 9/1978 | Beall | 374/25 |
| 4,334,505 A | 6/1982 | Jablin | |
| 4,482,005 A | 11/1984 | Voorhees | |
| 4,568,874 A * | 2/1986 | Kramer et al. | 324/688 |
| 5,493,865 A * | 2/1996 | Wohlwend | 62/51.1 |
| 5,813,541 A * | 9/1998 | Mottram | 209/2 |
| 5,865,913 A | 2/1999 | Paulin et al. | |
| 6,332,325 B1 | 12/2001 | Monfort | |
| 6,619,383 B2 * | 9/2003 | Squires | 165/84 |
| 6,679,067 B1 | 1/2004 | Pate et al. | |
| 6,694,997 B2 * | 2/2004 | Reyman | 137/39 |

* cited by examiner

*Primary Examiner* — J M Saint Surin
(74) *Attorney, Agent, or Firm* — Edward P. Dutkiewicz

(57) ABSTRACT

The system comprising an object to be tested, with the object has a structural resonant frequency. A vibration analyzer sends a signal through the object to a signal receiver. The signal receiver sends the data to a processor and a data storage device. A cooling chamber is used to cool the object to a specified temperature, and then allows the object to return to ambient temperature. A second vibrational test is performed and the data is compared with the first vibrational test to determine the effectiveness of the thermal treatment of the object.

4 Claims, 2 Drawing Sheets

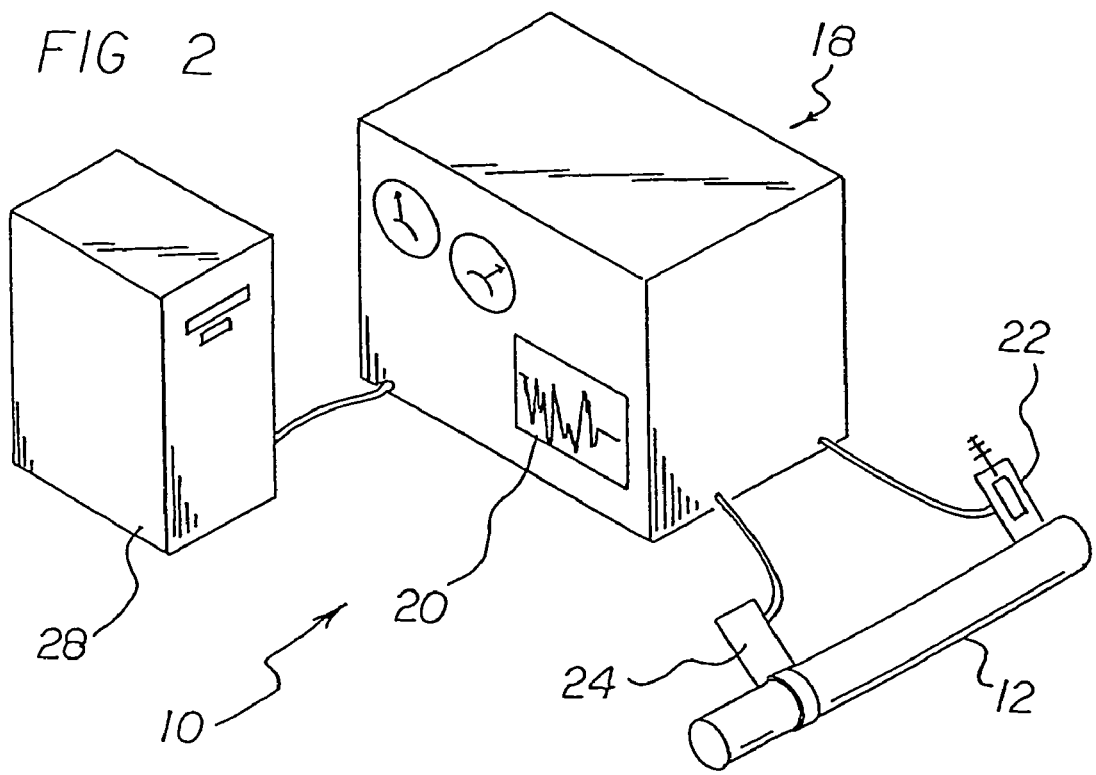
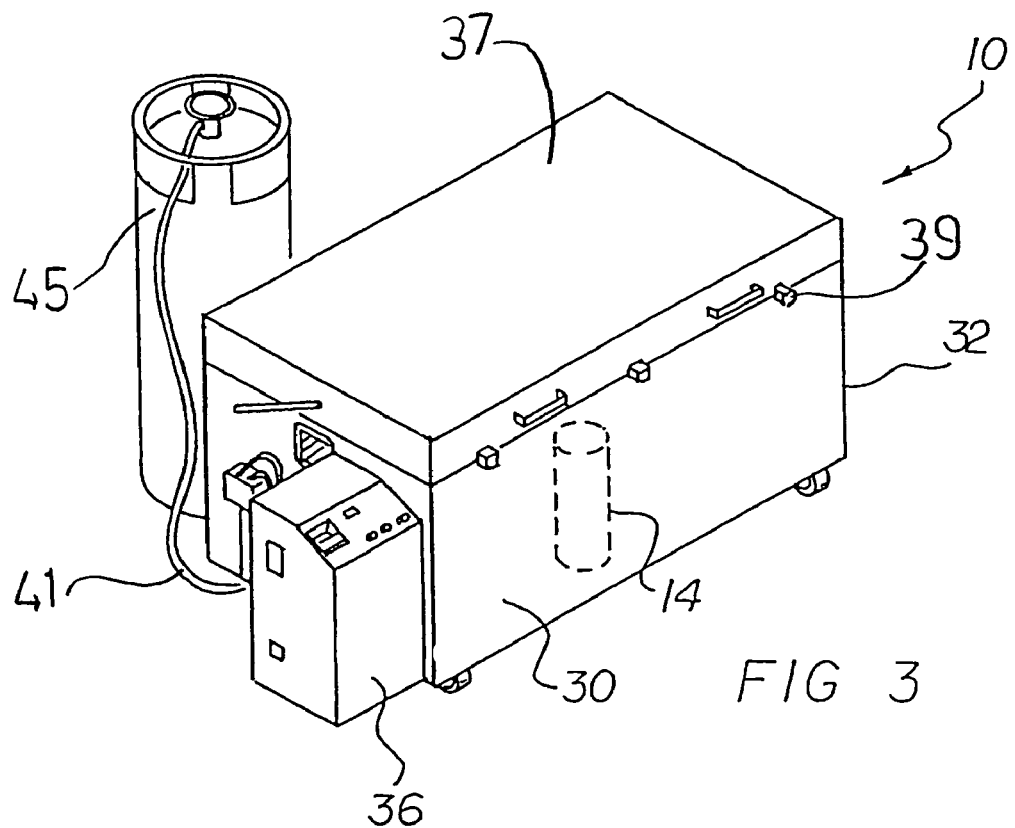

METALLURGIC TREATMENT AND VERIFICATION SYSTEM

RELATED APPLICATIONS

The present invention is a continuation-in-part of an application, bearing Ser. No. 11/651,152, filed on Jan. 9, 2007 now U.S. Pat. No. 7,464,593, and which is a continuation in part application of an application bearing Ser. No. 11/008,327, filed on Dec. 9, 2004 now abandoned. The present application claims the priority of the above referenced, applications.

BACKGROUND OF THE INVENTION

1. Field of the Invention

The present invention relates to a metallurgic treatment and verification system and more particularly pertains to using resonance to determine the effectiveness of cooling an object.

2. Description of the Prior Art

The use of other cooling methods without the use of object resonance is known in the prior art. More specifically, other cooling methods without the use of object resonance previously devised and utilized for the purpose of thermally treating an object to increase structural order are known to consist basically of familiar, expected, and obvious structural configurations, notwithstanding the myriad of designs encompassed by the crowded prior art which has been developed for the fulfillment of countless objectives and requirements.

While the prior art devices fulfill their respective, particular objectives and requirements, the aforementioned patents do not describe metallurgic treatment and verification system that allows using resonance to determine the effectiveness of cooling an object.

In this respect, the metallurgic treatment and verification system according to the present invention substantially departs from the conventional concepts and designs of the prior art, and in doing so provides an apparatus primarily developed for the purpose of using resonance to determine the effectiveness of cooling an object.

In addition, the novel manner for using temperature changes, is a departure from the prior art.

Therefore, it can be appreciated that there exists a continuing need for a new and improved metallurgic treatment and verification system which can be used for using resonance to determine the effectiveness of cooling an object. In this regard, the present invention substantially fulfills this need.

SUMMARY OF THE INVENTION

In view of the foregoing disadvantages inherent in the known types of other cooling methods without the use of object resonance now present in the prior art, the present invention provides an improved metallurgic treatment and verification system. As such, the general purpose of the present invention, which will be described subsequently in greater detail, is to provide a new and improved metallurgic treatment and verification system and method which has all the advantages of the prior art and none of the disadvantages.

To attain this, the present invention essentially comprises a metallurgic treatment and verification system for treating metals and compositions of metals. The system comprises several components, in combination.

First provided is an object to be tested. The object has a structural resonant frequency.

Next provided is a vibration analyzer. The vibration analyzer has an information generation subassembly comprising a signal sending component and a signal receiving component. The signal sending component is one of the class of sending components that includes a striking member, a vibratory member and a audio signal member for sending a signal through the object to be tested.

The vibration analyzer also has a signal receiving component for receiving the signal and generating data. The vibration analyzer has a data collection subsystem for receiving and storing the data received from the information generation subassembly. The data collection subsystem is coupled to the information generation subassembly.

Next provided is a chamber. The chamber has an enclosed space therein for receiving an object to be treated. The chamber is able to bringing the temperature of the object to a first specified temperature and keeping that object at that first temperature for a specified period of time. The chamber also is capable of allowing the object contained therein to have the object temperature changed from the first temperature to an ambient temperature. The change in temperature, either upwards or downwards, is determined by the physical characteristics of the objects, and the temperature rate of change is not controlled in any manner.

Lastly provided is at least one temperature cycle. The temperature cycle is the process of changing the temperature of an object to a prescribed temperature for a specified length of time and then returning the temperature of the object to ambient temperature.

This application also describes a method for treating metals and verifying the treatment. The method comprises several steps, in combination.

The first step is providing an object to be tested. The object has a structural resonant frequency.

The next step is providing a vibration analyzer having an information generation subassembly comprising a signal sending component and a signal receiving component. The vibration analyzer may be applied to the object to be tested. The sending component sends a signal through the object and the receiving component picks up the signal after it has passed through the object.

The next step is providing a first vibrational test utilizing the vibration analyzer on the object whereby a first data set is generated for the object being tested. The first test result establishes a baseline for the resonance of the object.

The next step is providing a chamber having an enclosed space therein for receiving an object that is to have its temperature changed and then returned to ambient temperature, with the temperature of the object determined by the physical properties of the object, that is, the temperature is not "ramped up" or "ramped down" in any manner.

The next step is providing a second vibrational test of the object that had been cooled and returned to ambient temperature. The same vibration analyzer is used. The second vibrational test generates a second data set. The second data set is stored in the data collection subsystem. The first data set may then be compared to the second data set.

The last step is providing at least one cycle of a temperature change of the object. A cycle comprises the process of changing the temperature of an object to a prescribed temperature for a specified length of time and then returning the cooled object to ambient temperature.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved metallurgic treatment and verification system which has all of the advantages of the prior art other cooling methods without the use of object resonance and none of the disadvantages.

It is another object of the present invention to provide a new and improved metallurgic treatment and verification system which may be easily and efficiently manufactured and marketed.

It is further object of the present invention to provide a new and improved metallurgic treatment and verification system which is of durable and reliable constructions.

An even further object of the present invention is to provide a new and improved metallurgic treatment and verification system which is susceptible of a low cost of manufacture with regard to both materials and labor, and which accordingly is then susceptible of low prices of sale to the consuming public, thereby making such metallurgic treatment and verification system economically available to the buying public.

Even still another object of the present invention is to provide a metallurgic treatment and verification system for using resonance to determine the effectiveness of changing the temperature of an object.

Lastly, it is an object of the present invention to provide a new and improved metallurgic treatment and verification system and method. The system comprising several components in combination.

First provided is an object to be tested. The object has a structural resonant frequency. Next provided is a vibration analyzer having a signal sending component and a signal receiver. Lastly provided is a temperature changing chamber having an enclosed space therein. The method comprises performing a first vibrational test on an object, and then changing the temperature of the object. The temperature of the object is changed to a first specific temperature for a specified amount of time and then returned to ambient temperature. A second vibrational test is performed and the data is compared with the first vibrational test to determine the effectiveness of the thermal treatment of the object.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

In FIG. 1, the first temperature change is a cooling of the object.

FIG. 2 shows a perspective view of the analyzer component of the system.

FIG. 3 is a perspective view of the chamber. The object to be treated is located within the chamber.

The same reference numerals refer to the same parts throughout the various Figures.

DESCRIPTION OF THE PREFERRED EMBODIMENT

Figure 1:
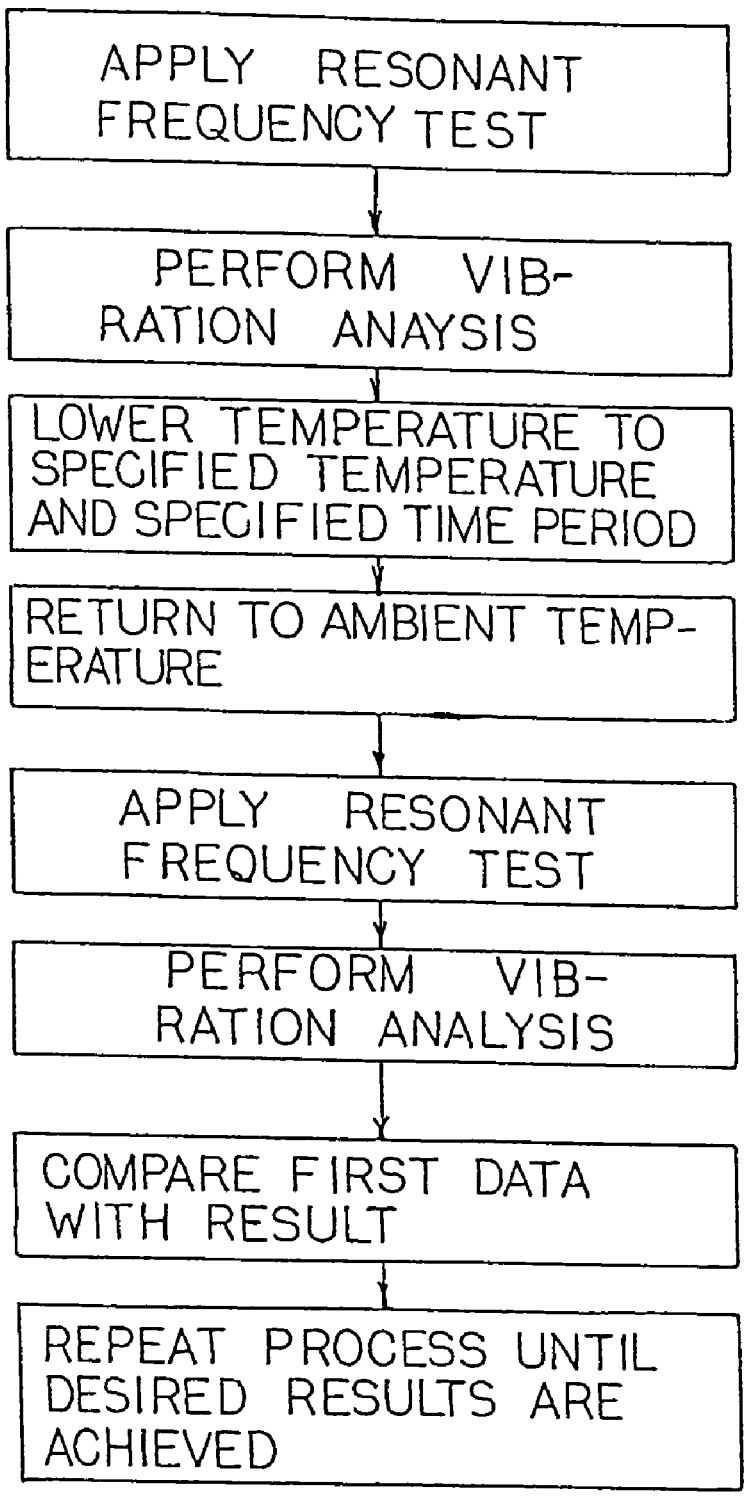
FIG. 1 is a flow chart of the steps of the process herein described.

With reference now to the drawings, and in particular to FIG. 1 thereof, the preferred embodiment of the new and improved metallurgic treatment and verification system embodying the principles and concepts of the present invention and generally designated by the reference numeral 10 will be described.

The present invention, the metallurgic treatment and verification system 10 is comprised of a plurality of components. Such components in their broadest context include a vibrational analyzer having a sending and receiving unit, a thermal cycling apparatus, and a data base to compare the results of the vibrational tests. Such components are individually configured and correlated with respect to each other so as to attain the desired objective.

First provided is an object 12, 14 to be tested. The object has a structural resonant frequency. The object has a first end and a second end. The identification of an "end" of an object us used to denote an area of the object. In the instance of a bar of metal, the first end is one end of the metal bar, and the second end is the opposing end of the metal bar. In the case of a ball shaped, or round, object, the first end is a point on the surface of the ball, and the second end is a point generally opposite of the first end on the surface of the ball.

The object may be made of metal, an alloy of metal, or a combination of metals. The object may also be made of any substance that may be cooled to extreme temperatures, such non-metals and synthetics. Inherent in any article are physical properties which govern the ability of the object to warm or cool in a particular matter. The cooling rate may be linear or the cooling rate may be exponential. The cooling rate, in this application, is the degree change of the object per unit of time. Cooling rate may be influenced by the size and shape of the object, as well as the mass of the object.

For example, the time it takes to cool a first object, being a sheet of aluminum, having the dimensions of 6 inches in width by 4 inches in length by $\frac{1}{16}$ of an inch in thickness will be less than it takes to cool a second object, being a block of aluminum having the dimensions of 6 inches in width by 4 inches in length by 8 inches in thickness, because of the greater mass of the second object to be cooled. While the temperature change of the density of the material is identical, the shape and size of the object causes the second item to take longer to cool. By allowing the item to cool, and warm, at its own inherent rate, the present device avoids any ramping or controlling of change of temperature within the chamber. Simplistically stated, the objects are exposed to a temperature in the range of about −280 degrees Fahrenheit to about −320 degrees Fahrenheit until the object attains the temperature of the environment of the chamber, and then the cooling material is allowed to dissipate, and the item then warms at the rate inherent to the object itself, and the environment within the chamber.

Next provided is a vibration analyzer 18. The vibration analyzer may be any one of the commercially available vibration analyzers and may have a display screen 20. The vibration analyzer has an information generation subassembly comprising a signal sending component 22 and a separate signal receiving component 24. The signal sending component is one of the class of sending components that includes a striking member, a vibratory member and a audio signal member for sending a signal through the object to be tested. Any way of generating a vibration, within the object to be tested, would be applicable.

The vibration analyzer also has a signal receiving component for receiving the signal and generating data. The signal receiving component couples with the object to be tested. The vibration analyzer has a data collection subsystem 28, such as a computer or other memory device, for receiving and storing the data received from the information generation subassembly. The data collection subsystem is coupled to the information generation subassembly. The coupling between the data collection subsystem and the generation subassembly may be electronic, radio frequency or light carried. The data may be digital or analogue. The data collector subsystem and the generation subassembly may be hard wired together.

The vibrational analysis is first performed on the object to be cooled. The vibrational test is done in an area remote from the cooling chamber, as shown in FIG. 2, though the vibrational test may be done within the cooling chamber. If the vibrational test is done within the chamber, the vibrational testing equipment would have to be removed from the chamber before the cooling of the object.

In performing the vibrational analysis of an object, the signal sending component is operationally coupled to the first end of the object and the signal receiving component is operationally coupled to the second end of the object. In this manner the signal is transmitted through the object along and through most of the mass of the object. In the case of a ball shaped object, the signal sending component would be operationally coupled to the surface of the ball, and the signal receiving component would be operationally coupled to the opposite surface of the ball.

Preferably, the vibrational test is done in a location apart from the cooling chamber, so that vibration occurs on the exterior of the cooling chamber, and not within the cooling chamber.

Next provided is a chamber 30 having an outer wall 32 and a control panel 36. In the preferred embodiment the chamber is a cooling chamber 30. In other embodiments the chamber may also be a heating chamber. In still other embodiments, the chamber may have both heating and cooling components, so that an object may be heated or cooled, depending on the material of the object. The chamber has a lid 37, which forms a sealed interior cavity, when closed. The chamber lid has associated latches 39, to lock the lid down, in position. The chamber has an associated circulating fan which circulates the coolant within the interior cavity of the chamber. A coolant inflow tube 41 couples a tank 45 to the cavity of the chamber. The flow of the coolant is controlled, either on or off, by the control panel, coupled to the chamber.

One skilled in the art would also recognize that the presence of heating elements, or the reference to heating may mean that an object is at a first, lower, temperature and then raised to a second, higher, temperature. Such is the case when an object is cooled to minus 300 degrees Fahrenheit and then the temperature is raised to minus 100 degrees Fahrenheit.

The cooling chamber has an enclosed space therein for receiving an object 12, 14 to be cooled. The cooling chamber may be any one of the commercially available cooling chambers. The cooling chamber is able to lower the temperature of the object to a first specified temperature for a first specified period of time. The first specified time period may vary from a second to one hundred hours.

Key to the heating or cooling of the object is the mass of the object. While commercially available cooling chambers control rise and descent of temperature using heaters and other means, the present invention departs from this type of control, or ramping, and instead, contrary to the previous teachings, relies on the mass of the object that is placed within the chamber to dictate the time it takes to cool an object. Simply put, a thin object having a small amount of mass, that is thermally conductive, such as aluminum, will have a rapid temperature drop when cooling is commenced. Alternatively, the same object will rise in temperature much faster than a more dense, or larger object, that is less thermally conductive.

In this invention control is merely the institution of the heating or cooling cycle. The rate of change of the temperature of the object is inherent to the object itself. As expected, the change of temperature in either a positive or negative direction, may be linear, exponential, or irregular, depending on the object being treated. The cooling chamber also is capable of allowing the cooled object contained therein to be brought from the cooled temperature to ambient temperature at a controlled specified rate.

Another difference, and an improvement over the prior art, is that the present invention may also return an object to ambient temperature by ambient temperature affecting the interior of the chamber, while the chamber remains closed. Simply put, the chamber remains closed while the heat transfer from without the chamber permeates the walls of the chamber, and warms the inside. This keeps moisture from entering the chamber, and therefore prevents the onset of rust in iron based objects.

In another embodiment, the chamber may be cooled liquid nitrogen and the warmed with a warmer gas, such as gaseous nitrogen, or carbon dioxide. This process would both facilitate warming of the object withing the chamber from sub-zero temperature to ambient, and would exclude moisture. As previously stated, the rate of the heating or cooling of an object would ultimately be determined by the object itself, and its mass.

Lastly provided is at least one cycle. In the preferred embodiment the cycle is referred to as a cooling cycle. The cooling cycle is the process of cooling an object to a first prescribed temperature for a first specified length of time and then the object returns to an ambient temperature. The cooling and the returning of the cooled object to ambient temperature is controlled, or determined by the physical characteristics of the object. The rate of temperature change within the chamber is not controlled so that the temperature change is at a specific degree Fahrenheit per minute ramp. In the preferred embodiment heat is not applied to the interior of the chamber, but ambient temperature is allowed to be transferred through the walls of the chamber, thereby warming the interior of the chamber, and the object.

In alternate embodiments a cycle may comprise the changing of the temperature of an object to a first temperature for a specified amount of time and then changing the temperature of an object to a second temperature for a second specified amount of time. The second specified time may range from one second to as much as one hundred hours. The object may then be returned to ambient temperature, or the object may be returned to the first temperature, and the process repeated any number of times before the object is returned to ambient temperature. It should be noted that there may be third, fourth and even fifth specified temperatures, depending on the object to be treated.

There may be more than one cooling cycle employed for an object. The pre-cooling data will be compared with the post-cooling data and the results will determine if additional cooling cycles are needed to achieve the desired results. As data is acquired, the data may be used to predetermine what the end desired result should be or should be expected to be. The inability to have an object reach the desired post cooling result may indicate a latent defect in the object.

It is further anticipated that the data collected from multiple samples of varying metals and object will form a data base that will allow a user to pre-cool test an object to determine if that object falls within the bounds of the data collected. Simply put, this data base may allow a user to test and predict if an object is free of defects, prior to any cooling cycling. The data base may also provide information to a user that would enable the user to skip any cooling treatment based on the findings of the pre-cooling test.

Until this time there has been debate as to whether cooling is beneficial or not. Advocates of cooling cite the advantages of increased tensile strength, increased elongation and the increased yield of cold treated objects. The implementation of a pre-cooling and post-cooling test, along with the compilation of data, will provide much needed information in this regard.

It has been shown that this new method of cooling is superior to the old method, that entails cooling an object to about minus 300 degrees Fahrenheit for a specified period of time and then allowing the object to return to ambient temperature. It has been shown that the heating the object to a temperature above ambient temperature accomplishes little, if any, structural improvement or integrity of the object. The present method produces an object that has increased yield, increased tensile strength and increased elongation. The present invention is an improvement over the prior art in that now a user can quantitatively ascertain the changes in an object subject to intense cold, without destroying the object.

This application also describes a method for treating metals and verifying the treatment. The method comprises several steps, in combination.

The first step is providing an object to be tested. The object has a structural resonant frequency. The object also has physical and material characteristics, which determine the overall rate of temperature change of the object as it is warmed or cooled.

The next step is providing a vibration analyzer having an information generation subassembly comprising a signal sending component and a signal receiving component. The vibration analyzer may be applied to the object to be tested. The testing is done at a location remote from the cooling chamber.

The sending component sends a signal through the object and the receiving component picks up the signal after it has passed through the object.

The next step is providing a first vibrational test utilizing the vibration analyzer on the object whereby a first data set is generated for the object being tested. The data is stored in a data storage device, such as a computer processor, or a computer disc. The first test result establishes a baseline for the resonance of the object.

A user may first scribe the object with a mark that indicates a pre-cooling test. The object is then tested and the results stored.

The next step is providing a cooling chamber having an enclosed space therein for receiving an object that may be cooled as disclosed above, and then allowed to return to ambient temperature. A cooling cycle comprises the process of cooling an object to a prescribed temperature for a specified length of time and then allowing the object to return to ambient temperature. As stated above, the cooling cycle may also be the cooling of an object to a first temperature and then allowing the temperature of the object to rise to a second temperature and then cooling the object to the first temperature and then allowing the temperature of the object to rise to ambient temperature. The object is cooled to a specified temperature and kept at that temperature for a specified time. The object then returns to ambient temperature. The lowest temperature used in the cooling chamber is approximately −392 degrees F. It should be recognized that each alloy has a range in which the cooling has the maximum effect. The temperature range differs for various metals and alloys. For example, copper alloy can be cold treated within a range of between about minus 110 degrees F. to about minus 190 degrees F.

The next step is providing a second vibrational test of the object that had been cooled and returned to ambient temperature. The same vibration analyzer is used, and is, like the first vibrational test, done at a location remote from the cooling chamber. The second vibrational test generates a second data set. The second data set is stored in the data collection subsystem which holds the first date set. The first data set may then be compared to the second data set, and changes between the two data sets may be noted and recorded.

The object may be inscribed with another mark demonstrating the success of the cooling process. The mark may also demonstrate the test outcome by stating the approximate resonant, or vibration, frequency.

Thermal treatment of metals is known in the art. No one, to the present, has, however, linked resonant frequency with thermal treatment. This application describes how resonant frequency, also known as vibration frequency, can be used to determine if cooling has had the desired effect on an object. As more and more tests are done, a large data base is formed, covering many, if not all, forms of alloys, combinations of metals, and synthetic materials. The data can be utilized to determine if the object that is thermally treated has latent defects, that become evident when the object is subject to pre and post cooling vibrational analysis.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A metallurgic treatment and verification system comprising, in combination:
   an object to be tested, the object having a structural resonant frequency and physical;
   a cooling chamber having an enclosed space therein wherein the object is cooled and then allowed to return to ambient temperature at a rate determined by the physical characteristics of the article, with the cooling chamber being able to lower the temperature of an object for a specified period of time at a specified cooled temperature, the cooling chamber also being capable of allowing the cooled object contained therein to be brought from the cooled temperature to ambient temperature, with the physical characteristics of the object determining the rate of heating and cooling.

2. A metallurgic treatment and verification system for treating metals and compositions of metals comprising, in combination:
   an object to be tested with the object having a structural resonant frequency and physical characteristics;
   a vibration analyzer having an information generation subassembly comprising a signal sending component and a signal receiving component, the signal sending component being one of the class of sending components that includes a striking member, vibratory member and a audio signal member for sending a signal through the object to be tested, the vibration analyzer also having a signal receiving component for receiving the signal and generating data, the vibration analyzer having a data collection subsystem for receiving and storing the data received from the information generation subassembly, with the data collection subsystem being coupled to the information generation subassembly;
   a cooling chamber having an enclosed space therein for receiving an object to be cooled, the cooling chamber being able to lower the temperature of an object for a specified period of time at a first specified cooled temperature, the cooling chamber also being capable of allowing the temperature of the cooled object contained therein to change from the first cooled temperature to ambient temperature with the rate of temperature change being determined by the physical characteristics of the object;
   the vibration analyzer being located remote from the cooling chamber; and
   at least one cooling cycle, the cooling cycle being the process of cooling an object at ambient temperature to a prescribed temperature for a specified length of time and then allowing the object to return to ambient temperature.

3. A method for treating metals and verifying the treatment, comprising, in combination:
   having an object to be tested, with the object having a structural resonant frequency and physical characteristics;
   having a cooling chamber having an enclosed space therein for receiving the object that is cooled and then allowed to return to ambient temperature with the rate of change of temperature being determined by the physical characteristics of the object;
   cooling the object, using least one cooling cycle, the cooling cycle being the process of cooling an object to a prescribed temperature for a specified length of time and then allowing the temperature of the object to return to ambient temperature at a rate determined by the physical characteristics of the object.

4. A method for treating metals and verifying the treatment as set forth in claim 3, the system further comprising:
   having a vibration analyzer having an information generation subassembly comprising a signal sending component and a signal receiving component whereby the vibration analyzer signal sending component and a signal receiving component may be applied to the object to be tested;
   performing a first vibrational test utilizing the vibration analyzer on the object whereby a first data set is generated for the object being tested, the first vibrational test being performed at a location remote from the cooling chamber;
   the cooling chamber having a lid, with the lid and the chamber having an air gap there between;
   performing a second vibrational test of the object that had been cooled and then allowed to return to ambient temperature using the vibration analyzer, the second vibrational test generating a second data set with the second data set being stored in the data collection subsystem whereby the first data set may be compared to the second data set, the second vibrational test being performed at a location remote from the cooling chamber; and
   comparing the first date set with the second data set to determine the effectiveness of the cooling cycle on the object.

* * * * *